United States Patent [19]

Moran et al.

[11] 4,260,755
[45] Apr. 7, 1981

[54] NOVEL 6-PHENYL AND SUBSTITUTED 6-PHENYL-1,2,4-TRIAZOLO[4,3-B]PYRIDAZINES

[75] Inventors: Daniel B. Moran, Suffern; Jay D. Albright, Nanuet, both of N.Y.

[73] Assignee: American Cyanamid Company, Stamford, Conn.

[21] Appl. No.: 89,440

[22] Filed: Oct. 31, 1979

[51] Int. Cl.³ .................. C07D 237/00; A61K 31/50
[52] U.S. Cl. ..................... 544/236; 424/250
[58] Field of Search ......................................... 544/236

[56] References Cited

U.S. PATENT DOCUMENTS

| 3,940,248 | 2/1976 | Yamaguchi et al. | 544/236 |
| 4,112,095 | 9/1978 | Allen, Jr. et al. | 544/236 |
| 4,117,130 | 9/1978 | Allen, Jr. et al. | 424/250 |

OTHER PUBLICATIONS

H. Yale, J. Med. & Pharm. Chem., vol. 1, No. 2 (1959), pp. 121-133, The TrifluoromethylGroup in Medicinal Chemistry, P. Dalla Croce, Chem. Abstracts 84: 135592Z (1976).

Primary Examiner—Donald G. Daus
Assistant Examiner—M. C. Eakin

[57] ABSTRACT

This disclosure describes novel 6-phenyl and substituted 6-phenyl-1,2,4-triazolo[4,3-b]pyridazines and their use as anxiolytic agents.

6 Claims, No Drawings

NOVEL 6-PHENYL AND SUBSTITUTED 6-PHENYL-1,2,4-TRIAZOLO[4,3-B]PYRIDAZINES

BRIEF SUMMARY OF THE INVENTION

This invention relates to new organic compounds and, more particularly, is concerned with novel 6-phenyl and substituted 6-phenyl-1,2,4-triazolo[4,3-b]pyridazines which may be represented by the following structural formula:

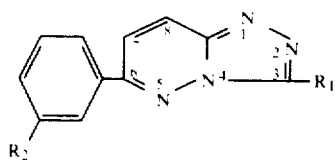

wherein $R_1$ is selected from the group comprising, CHO, $CH_2Cl$, $CHCl_2$, $CCl_3$, $CH_2OH$, $CH_2O$-lower alkyl ($C_1$-$C_3$), $CH_2F$, $CHF_2$, $CF_3$, CN and $CO_2$-lower alkyl ($C_1$-$C_3$); $R_2$ is selected from the group consisting of hydrogen, fluoro, chloro and trifluoromethyl.

DESCRIPTION OF THE INVENTION

The 6-phenyl and substituted 6-phenyl-1,2,4-triazolo[4,3-b]pyridazines of the present invention are in general, colorless, tan or pale yellow crystalline solids having characteristic melting points and spectral properties. They are soluble in organic solvents such as lower alkanols, dimethylsulfoxide, and N,N-dimethylformamide. They are, however, generally insoluble in water.

The 3-monohalomethyl, 3-dihalomethyl and 3-trihalomethyl-1,2,4-triazolo[4,3-b]pyridazines of this invention are prepared by reaction of 6-phenyl and substituted 6-phenyl-3-hydrazinopyridazines with mono, di or tri chloro or fluoro acetic acids or with mono, di or tri chloro or fluoro acetyl chlorides. Alternatively, the 6-phenyl and substituted 6-phenyl-3-hydrazinopyridazines are reacted with mono, di or tri chloro or fluoro acetic anhydrides to give the products of the invention.

Products containing a 3-monohalomethyl, 3-dihalomethyl and a 3-trihalomethyl substituent are prepared as shown in Schemes I, where X is chloro and fluoro and $R_2$ is as previously defined.

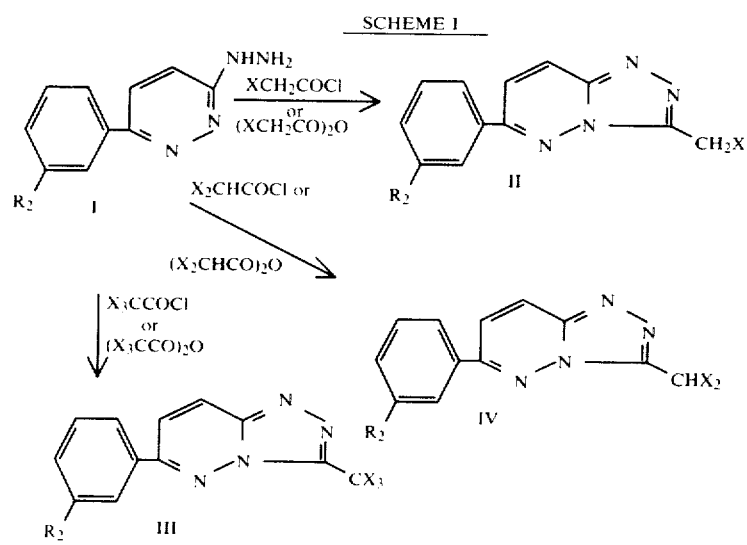

SCHEME I

SCHEME II

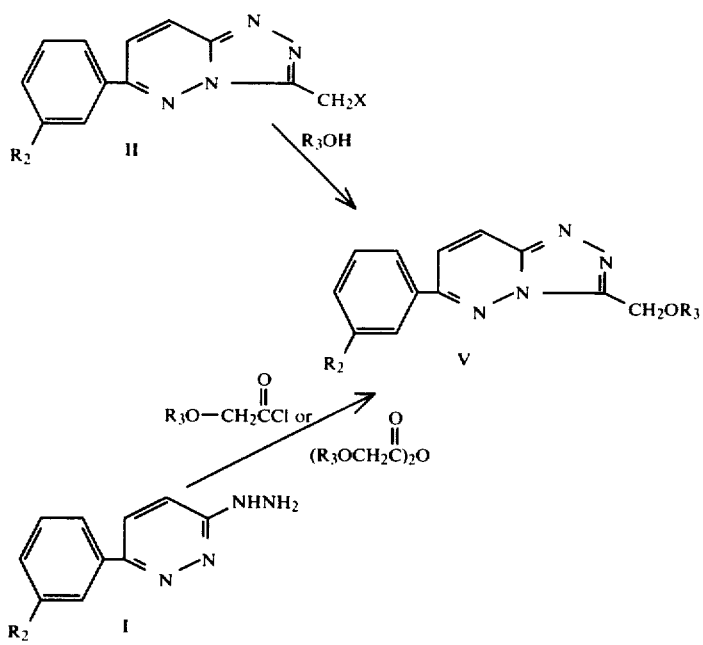

The novel 3-lower alkoxymethyl 1,2,4-triazolo[4,3-b]pyridazines of this invention are prepared by reaction of a 3-halomethyl derivative II with the anion of a lower alkanol ($R_3OH$) wherein $R_3$ is a lower alkyl group of one to 3 carbon atoms in an inert solvent or preferably in excess lower alkanol as solvent. Alternatively, a lower alkoxy acetyl chloride or anhydride is reacted with a 6-phenyl or substituted-phenyl 3-hydrazinopyridazine (I) to give the products of formula V as shown in Scheme II. Products of this invention wherein $R_1$ is —$CO_2$ lower alkyl ($C_1$–$C_3$) are prepared by reaction of a 3-hydrazinopyridazine of formula I with a lower alkyl ($C_1$–$C_3$) oxalyl chloride to give the derivatives of formula VI.

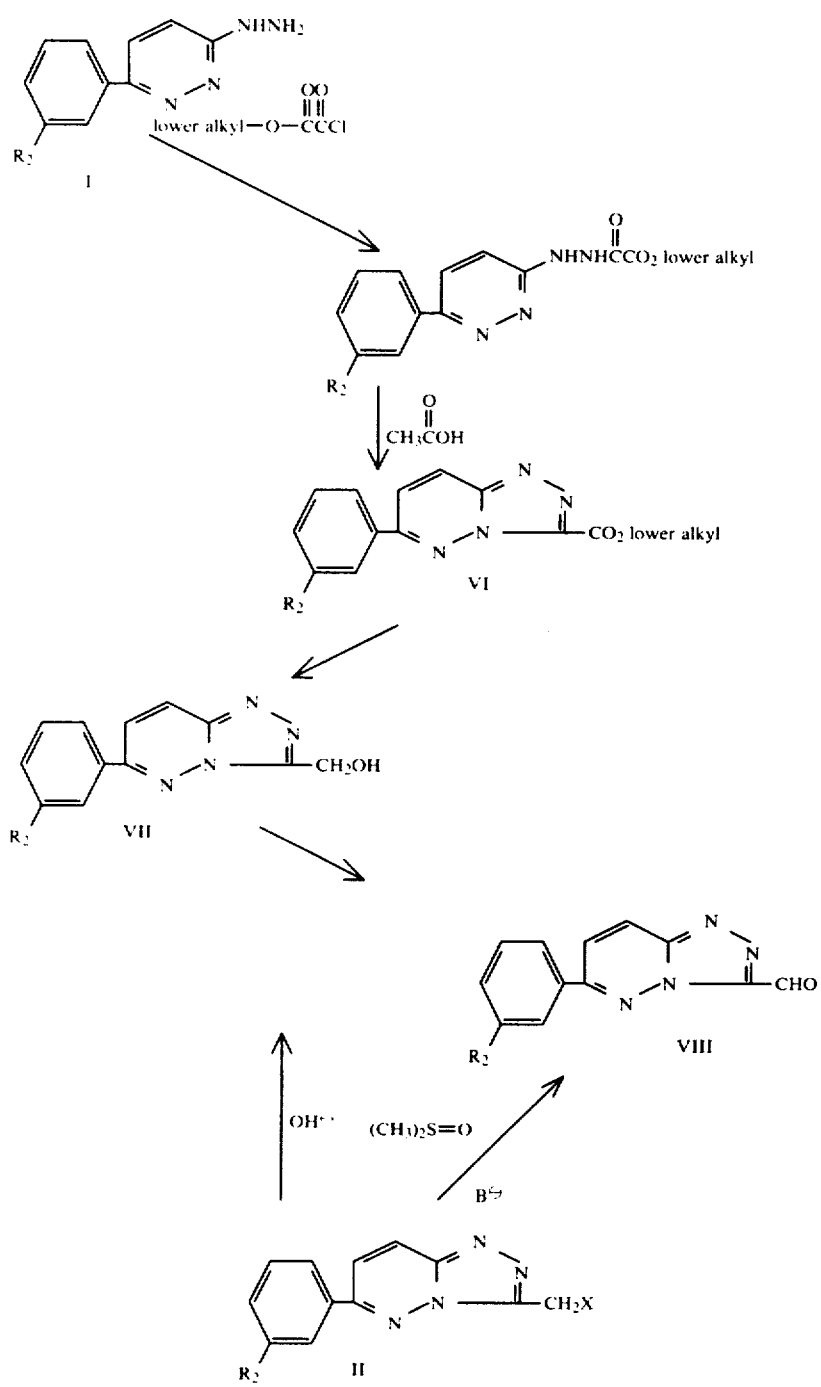

Novel compounds of this invention wherein $R_1$ is $CH_2OH$ and CHO may be prepared as shown in the above reaction schemes. Reaction of a 3-halomethyl derivative II wherein X is halogen with aqueous base or with water under solvolytic conditions in the presence of silver nitrate gives the 3-hydroxymethyl derivatives VII. Alternatively, 3-lower alkoxy carbonyl derivatives VI may be reduced with appropriate metal hydrides or sodium in liquid ammonia to give the novel compounds VII. Oxidation of 3-hydroxymethyl derivatives VII with dimethyl sulfoxide-acetic anhydride and similar reagents gives the 3-carboxaldehyde compounds VIII. Reaction of 3-halomethyl-1,2,4-triazolo[4,3-b]pyridazines of structural formula II with dimethyl sulfoxide in the presence of a base such as pyridine gives the 3-carboxaldehyde derivatives VIII.

The novel compounds of the present invention possess central nervous system acitivity at non-toxic doses and as such are useful as anxiolytic agents. That is, they produce certain responses in standard tests with laboratory animals which are known to correlate well with relief of anxiety in man.

The anti-anxiety properties of the novel compounds of the present invention have been established in a test which indicates anxiolytic activity by the measure of protection from convulsions resulting from the administration of pentylenetetrazole. Single or graded dose levels of the test compounds were administered orally or intraperitoneally in a 2% starch vehicle, containing 0.5% v/v polyethylene glycol and one drop of polysorbate 80 to groups of at least 4 rats. At 30 or 60 minutes, the rats were treated intravenously with pentylenetetrazole at a dose of 23 mg./kg. of body weight. This dose is estimated to cause clonic seizures in 99% of unprotected rats. The test compounds are considered active if they protect 50% or more of the rats from clonic seizures. It has been reported [R. T. Hill and D. H. Tedeschi, "Animal Testing and Screening Procedures in Evaluating Psychotropic Drugs" in "An Introduction to Psychopharmacology", Eds. R. R. Rech and K. E. Moore, Raven Press, New York, pp. 237-288 (1971)] that there is a high degree of correlation between antagonism of pentylenetetrazole seizures in rats and antianxiety effects in higher warm-blooded animals. The following representative compounds of the present invention have been shown to possess anxiolytic activity when tested as described above.

3-(Methoxymethyl)-6-phenyl-1,2,4-triazolo[4,3-b]pyridazine 3-(Methoxymethyl)-6-[3-(trifluoromethyl)phenyl]-1,2,4-triazolo[4,3-b]pyridazine

BRAIN-SPECIFIC BENZODIAZEPINE RECEPTOR BINDING ASSAY

Another test utilized for the determination of anxiolytic activity is the measurement of the ability of test compounds to inhibit the binding of tritiated benzodiazepines to brain-specific receptors of warm-blooded animals. A modification of the method described by R. F. Squires et al. Nature, 266, No. 21, pg. 732, (April, 1977) and H. Mohler et al. Science, 198, pg. 849, (1977) was employed.

Male albino rats (Wistar strain, weighing 150-200 g. each) were obtained from Royalhart Farms. $^3$H-Methyl-diazepam (79.9 Ci/mmol) and $^3$H-methylflunitrazepam (84.3 Ci/mmol) were obtained from New England Nuclear. The test compounds were solubilized in either dimethylformamide, acetic acid, ethanol or hydrochloric acid.

Whole cortex of rats was homogenized gently in 20 volumes of ice-cold 0.32 M. sucrose, centrifuged twice at 1000 g for 10 minutes and then recentrifuged at 30,000 g for 20 minutes to produce a crude $P_2$-synaptosomal fraction. The $P_2$-fraction was either: (1) resuspended in twice the original volume in hypotonic 50 mM. Tris.HCl (pH 7.4), or (2) resuspended in one-half the original volume in hypotonic 10 mM. Tris.HCl (pH 7.4) and frozen ($-20°$ C.) until time of use. Frozen $P_2$ preparations were thawed and resuspended in four times the original homogenizing volume at time of assay.

The binding assay consisted of 300 μl. of the $P_2$-fraction suspension (0.2-0.4 mg. protein), 100 μl. of test drug and 100 μl. of $^3$H-diazepam (1.5 nM., final concentration) of $^3$H-flunitrazepam (1.0 nM., final concentration) which was added to 1.5 ml. of 50 mM. Tris.HCl (pH 7.4). Non-specific binding controls and total binding controls received 100 μl. of diazepam (3 μM. final concentration) and 100 μl. of deionized water, respectively, in place of the test compound. Incubation for 30 minutes proceeded in ice and was terminated by filtration, under vacuum, through Whatman GF/C glass fiber filters. The filters were washed twice with 5 ml. of ice-cold 50 mM. Tris.HCl (pH 7.4) and placed in scintillation vials. After drying at 50°-60° C. for 30 minutes, 10 ml. of Beckman Ready-Solve HP was added and the radioactivity determined in a Beckman Scintillation Counter.

Compounds which exhibited the ability to inhibit $^3$H-benzodiazepine binding by $\geq 20\%$ were considered to be active. Inhibition of binding was calculated by the difference between total binding and binding in the presence of test compound, divided by the total binding, X 100.

Representative compounds of the present invention which are active when tested by the $^3$H-benzodiazepine binding assay are:

3-(Chloromethyl)-6-phenyl-1,2,4-triazolo[4,3-a]pyridazine 3-(Chloromethyl)-6-[3-(trifluoromethyl)phenyl]-1,2,4-triazolo[4,3-b]pyridazine The compounds of the present invention may be administered to warm-blooded animals orally or parenterally, if desired and when so administered, may be considered as tranquilizing agents for therapeutically desirable treatment of anxiety in warm-blooded animals.

The dosage regimen can be adjusted to provide optimum therapeutic response. Thus, for example, several doses may be administered daily, or the dose may be reduced proportionately as indicated by the requirements of the particular therapeutic situation.

For therapeutic administration, the compounds of this invention may be incorporated with pharmaceutical carriers such as excipients and used, for example, in the form of tablets, troches, dragees, capsules, suspensions, emulsions, liquids, syrups, wafers, chewing gum or the like for oral administration.

Parenteral solutions and suspensions may be prepared for intramuscular or subcutaneous administration, and suppositories may be prepared for rectal administration. Such compositions and preparations should contain at least 0.1% of active component. The percentage in the compositions and preparations may, of course, be varied and may conveniently be between 2% to about 75% or more of the weight of the unit. The amount of anxiolytic active component in such therapeutically useful compositions or preparations is such that a suitable dosage of from about 3 mg. to about 100 mg./kg./day will be obtained.

Preferred compositions or preparations according to the present invention are prepared so that an anxiolytic dosage unit form contains between about 1.0 mg. and 100 mg. of the therapeutically active component.

The compositions of this invention are physiologically active as anxiolytic agents. As such, they can be incorporated in various pharmaceutical forms such as set forth immediately above, for immediate or sustained release, by combining with suitable pharmaceutical carriers. They may be in the form of dosage units for a single therapeutic dose or in small units for multiple dosages or in larger units for division into single doses.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed.

SPECIFIC DISCLOSURE

The following specific examples illustrate the preparation of the compounds of the present invention.

EXAMPLE 1

3-(Chloromethyl)-6-[3-((trifluoromethyl)-phenyl]-1,2,4-triazolo[4,3-b]pyridazine A mixture of 80.0 g. of 3-chloro-6-[3-trifluoromethyl)phenyl]pyridazine (prepared as in Example 11 of U.S. Pat. No. 4,112,095), 150 ml. of hydrazine monohydrate and 800 ml. of n-butyl alcohol is refluxed for 18 hours. The reaction mixture is concentrated free of solvent. The solid concentrate is filtered and washed with hexane several times to provide 110.0 g. of 3-hydrazino-6-[3-(trifluoromethyl)-phenyl]pyridazine as a cream colored solid.

To a chilled mixture of 17.5 g. of the preceding product in 300 ml. of tetrahydrofuran is added dropwise 5.48 ml. of chloroacetyl chloride. The reaction mixture is allowed to warm to room temperature and is stirred for 16 hours. The mixture is diluted with ether and filtered to collect a solid. The solid is stirred with saturated sodium bicarbonate solution, collected by filtration, and washed with water and dichloromethane to give 19.0 g. of 2-[6-(3-Trifluorophenyl)-3-pyradazinyl]hydrazide chloroacetic acid as cream colored crystals, m.p. 119°-121° C.

A mixture of 3.2 g. of the preceding compound and 50 ml. of glacial acetic acid is heated at reflux temperature for 3 hours. The solvent is removed in vacuo and the residue is dissolved in dichloromethane. This solution is filtered through a column of hydrous magnesium silicate. The eluent is concentrated, diluted with petroleum ether, cooled and filtered to yield 0.8 g. of the product of the Example as white crystals, m.p. 183°-185° C.

EXAMPLE 2

3-(Chloromethyl)-6-phenyl-1,2,4-triazolo[4,3-b]pyridazine

To a mixture of 16.9 g. of 3-hydrazine-6-phenylpyridazine in 250 ml. of tetrahydrofuran chilled in an ice bath, is added portionwise over 30 minutes, 7.24 ml. of chloroacetyl chloride in 50 ml. of tetrahydrofuran. After stirring one hour, the mixture is allowed to warm to room temperature and is stirred for 3 hours. The solvent is removed under reduced pressure and the residue partitioned between ether and saturated sodium bicarbonate solution. The mixture is filtered and the solid washed with sodium bicarbonate solution and with water to give 23 g. of a solid. The solid is recrystallized from dichloromethane-hexane to give 8.9 g. of crystals identified as 2-(6-phenyl-3-pyridazinyl) chloroacetic acid hydrazide, m.p. 133°-134° C.

A 24.65 g. amount of the preceding product prepared as described above and 300 ml. of acetic acid is heated at 145° C. for one hour. The mixture is treated with activated carbon and filtered. The solvent is removed and the residual oil is triturated with ether to give a solid which is filtered and washed with ether. The solid is dissolved in dichloromethane and filtered through a column of hydrous magnesium silicate. The eluent (first cut) gives 7.43 g. of crude product. A sample is purified by thick layer chromatography on a silica gel plate to give the product of the Examples as a solid which is recrystallized from dichloromethane-hexane to give crystals, m.p. 165°-166° C.

EXAMPLE 3

3-(Methoxymethyl)-6-phenyl-1,2,4-triazolo[4,3b-]pyridazine

To a solution of 0.89 g. of sodium methoxide in 200 ml. of methyl alcohol is added 3.4 g. of 3-(chloromethyl)-6-phenyl-1,2,4-triazolo[4,3-b]pyridazine. The reaction mixture is heated at reflux temperature for 18 hours then is treated with activated charcoal and filtered. The filtrate is evaporated to give a white solid. The solid is dissolved in methylene chloride and passed through a column of hydrous magnesium silicate. The eluent is concentrated and diluted with hexane to give 3.0 g. of white crystals. Recrystallization from methylene chloride-hexane gives the product of the Example as white crystals, m.p. 133° C.

EXAMPLE 4

3-(Methoxymethyl)-6-phenyl-1,2,4-triazolo[4,3-b]pyridazine

To a mixture of 0.01 mole of 3-hydrazino-6-phenylpyridazine in 25 ml. of dioxane is added 0.005 mole of methoxyacetyl chloride. The mixture is refluxed for 2 hours to give the product of the Example, m.p. 133° C.

EXAMPLE 5

3-(Methoxymethyl)-6-[3-(trifluoromethyl)phenyl]-1,2,4-triazolo[4,3-b]pyridazine

A mixture of 2.1 g. of 3-(chloromethyl)-6-[3-(trifluoromethyl)phenyl]-1,2,4-triazolo[4,3-b]pyridazine and 0.40 g. of sodium methoxide in 50 ml. of ethanol is refluxed for 24 hours. The solvent is removed under reduced pressure and the residue is dissolved in dichloromethane. The solution is filtered through a column of hydrous magnesium silicate. The eluent is concentrated and hexane added to give 1.4 g. of the product of the Example as crystals, m.p. 149°-150° C. Recrystallization from dichloromethane-hexane gives 0.6 g. of white crystals, m.p. 149°-151° C.

EXAMPLE 6

3-(Methoxymethyl)-6-[3-(trifluoromethyl)-phenyl]-1,2,4-triazolo[4,3-b]pyridazine To a mixture of 0.02 mole of 3-hydrazino-6-[3-(trifluoromethyl)phenyl]pyridazine in 50 ml. of dioxane is added 0.01 mole of methoxyacetyl chloride. The mixture is heated at reflux temperature for 4 hours, then is filtered. The filtrate is evaporated and the residue is crystallized from dichloromethane-hexane to give the product of the Example, m.p. 149°-150° C.

EXAMPLE 7

6-(3-Fluorophenyl)-3-(methoxymethyl)-1,2,4-triazolo[4,3-b]pyridazine

As for Example 4, 6-(3-fluorophenyl)-3-hydrazinopyridazine (prepared in a manner similar to that described in Example 1) is reacted with methoxyacetyl chloride to give the product of the Example.

EXAMPLE 8

6-(3-Chlorophenyl)-3-(methoxymethyl)-1,2,4-triazolo[4,3-b]pyridazine

As for Example 4, 6-(3-chlorophenyl)-3-hydrazinopyridazine (prepared as in Example 51 of U.S. Pat. No. 4,112,095) is reacted with methoxyacetyl chloride to give the product of the Example.

EXAMPLE 9

3-(Chloromethyl)-6-(3-fluorophenyl)-1,2,4-triazolo[4,3-b]pyridazine

As for Example 2, 6-(3-fluorophenyl)-3-hydrazinopyridazine (prepared in a manner similar to that described in Example 1) is reacted with chloroacetyl chloride to give the product of the Example.

EXAMPLE 10

3-(Chloromethyl)-6-(3-chlorophenyl)-1,2,4-triazolo[4,3-b]pyridazine

As for Example 2, 6-(3-chlorophenyl)-3-hydrazinopyridazine is reacted with chloroacetyl chloride to give the product of the Example.

EXAMPLE 11

6-Phenyl-3-(trifluoromethyl)-1,2,4-triazolo[4,3-b]pyridazine

To a mixture of 3.5 g. of 3-hydrazino-6-phenylpyridazine in 35 ml. of pyridine is added dropwise 6.3 g. of trifluoroacetic anhydride. The mixture is refluxed for 6 hours, cooled and the solvent removed under reduced pressure. The residue is dissolved in ethyl acetate and passed through a pad of hydrous magnesium silicate. The eluent is concentrated to a dark solid which is recrystallized twice from ethanol to give 2.0 g. of the product of the Example as crystals, m.p. 183°–184° C.

EXAMPLE 12

6-(3-Chlorophenyl)-3-(trifluoromethyl)-1,2,4-triazolo[4,3-b]pyridazine

As for Example 11, 6-(3-chlorophenyl)-3-hydrazinopyridazine is reacted with trifluoroacetic anhydride in refluxing pyridine to give the product of the Example.

EXAMPLE 13

6-(3-Fluorophenyl)-3-(trifluoromethyl)-1,2,4-triazolo[4,3-b]pyridazine

As for Example 11, 6-(3-fluorophenyl)-3-hydrazinopyridazine is reacted with trifluoroacetic anhydride in refluxing pyridine to give the product of the Example.

EXAMPLE 14

3-Cyano-6-[3-(trifluoromethyl)-phenyl]-1,2,4-triazolo[4,3-b]pyridazine

A mixture of 7.72 g. of 3-methyl-6-[3-(trifluoromethyl)phenyl]-1,2,4-triazolo[4,3-b]pyridazine, 17.6 ml. of N,N-diisopropylethylamine, 140 ml. of dioxane and 9.8 ml. of benzoyl chloride is heated at reflux temperature for 48 hours. The resulting mixture is evaporated in vacuo and the residue is partitioned between water and dichloromethane. The organic layer is separated, dried over anhydrous sodium sulfate and evaporated to give a dark solid. The solid is heated with ethanol and the resulting mixture is filtered to collect 10.6 g. of α-{[6-[3-(trifluoromethyl)phenyl]-1,2,4-triazolo[4,3-b]pyridazin-3-yl]methylene benzyl alcohol, benzoate (ester) as crystals. Recrystallization from methylene chloride gives cream colored crystals, m.p. 238°–240° C.

A mixture of 1.0 g. of the preceding compound, 10 ml. of water, 10 ml. of concentrated hydrochloric acid and 15 ml. of ethanol is heated on a steam bath for 18 hours. The mixture is cooled and filtered to collect a solid. The solid is washed with water to give 0.9 g. of off-white crystals. The material is recrystallized from ethanol-water to give 0.7 g. of 2-[6-[3-(trifluoromethyl)-phenyl]-1,2,4-triazolo[4,3-b]pyridazin-3-yl]acetophenone as off-white crystals, m.p. 215°–218° C.

A 0.38 g. amount of the above product is dissolved in 5 ml. of concentrated sulfuric acid at room temperature, then 0.35 g. of sodium nitrite is added and the mixture is allowed to stand at room temperature for one hour. The reaction mixture is poured into crushed ice/water and filtered. The filter cake is washed with water and air dried to give 0.4 g. of cream colored solid. The solid in 25 ml. of thionyl chloride is heated at the reflux temperature for 30 minutes then is allowed to stand at room temperature for 2 hours. The reaction mixture is stripped of volatiles, cooled with cracked ice and made alkaline with concentrated ammonium hydroxide. The mixture is extracted with methylene chloride. The combined extracts are dried over anhydrous sodium sulfate and evaporated to give 0.37 g. of a tan solid. The product is purified further by conventional preparative thin layer chromatography using silica gel plates and acetic acid/hexane (1:1) to afford a white solid. The solid is recrystallized from methylene chloride/hexane to give the product of the Example as white crystals, m.p. 184°–185° C.

EXAMPLE 15

6-[3-(Trifluoromethyl)phenyl]-1,2,4-triazolo[4,3-b]pyridazine-3-carboxylic acid, ethyl ester To a suspension of 15.24 g. of 3-hydrazino-6-[3-(trifluoromethyl)phenyl]pyridazine in 200 ml. of tetrahydrofuran, cooled in an ice bath is added dropwise, a solution of 9.84 g. of ethyl oxalyl chloride in 50 ml. of tetrahydrofuran over 30 minutes. The mixture is stirred at room temperature for 16 hours then the solvent is evaporated in vacuo. The residue is stirred with dichloromethane, and filtered. The solid is washed with dichloromethane and with hexane to give 15.0 g. of 2-[6-[3-(trifluoromethyl)phenyl]-3-pyridazinyl]hydrazide oxalic acid, ethyl ester as a cream colored solid, m.p. 193°–196° C.

A mixture of the preceding compound (15.0 g.) in 175 ml. of glacial acetic acid is heated at reflux temperature for ¼ hour and filtered through diatomaceous earth while hot. The filtrate is evaporated in vacuo. The residue is dissolved in dichloromethane and this solution is washed with an aqueous saturated sodium bicarbonate solution. The organic layer is dried over anhydrous sodium sulfate and the solvent is removed. The resulting residue is dissolved in a minimum volume of dichloromethane and hexane is added. Filtration gives 5.9 g. of the product of the Example as white crystals, m.p. 202°–204° C.

EXAMPLE 16

3-(Hydroxymethyl)-6-[3-(trifluoromethyl)-phenyl]-1,2,4-triazolo[4,3-b]pyridazine A mixture of 2.3 g. of 3-hydrazino-6-[3-(trifluoromethyl)phenyl]pyridazine, 188 g. of ethyl glycolate and 40 ml. of n-butyl alcohol is heated at reflux temperature for 18 hours. The mixture is evaporated in vacuo. To the residue is added dichloromethane and hexane. The mixture is filtered to give 2.0 g. of cream colored crystals. Recrystallization from ethyl acetate gives the product of the Example as off-white crystals, m.p. 224°–226° C.

EXAMPLE 17

3-(Hydroxymethyl)-6-[3-(trifluoromethyl)-phenyl]-1,2,4-triazolo[4,3-b]pyridazine A mixture of 7.76 g. of 3-chloro-6-[3-(trifluoromethyl)phenyl]pyridazine, 6.66 g. of hydroxyacethydrazide and 200 ml. of n-butyl alcohol is heated at reflux temperature for 18 hours. The mixture is evaporated in vacuo and the residue is triturated with dichloromethane-hexane. The mixture is filtered and the solid is recrystallized from ethyl acetate to give the product of the Example as off-white crystals, m.p. 224°–226° C.

EXAMPLE 18

3-(Hydroxymethyl)-6-[3-(trifluoromethyl)-phenyl]-1,2,4-triazolo[4,3-b]pyridazine A 1.0 g. sample of 3-(chloromethyl)-6-[3-(trifluoromethyl)phenyl]-1,2,4-triazolo[4,3-b]pyridazine is heated (50°–60° C.) in a mixture of acetone and water in the presence of silver nitrate. The mixture is filtered and the filtrate concentrated to give the product of the Example.

EXAMPLE 19

3-(Trifluoromethyl)-6-(3-trifluoromethylphenyl)-1,2,4-triazolo[4,3-b]pyridazine

A mixture of 1.4 g of 3-hydrazino-6-[3-(trifluoromethyl)phenyl]pyridazine and 3.0 g. of trifluoroacetic anhydride in 20 ml. of pyridine is refluxed for 16 hours. The mixture is concentrated under vacuum and the residue treated with aqueous sodium bicarbonate solution. The mixture is filtered and the solid dissolved in chloroform. The chloroform solution is dried over anhydrous sodium sulfate and hexane is added. Filtration gives 0.7 g. of the desired product as crystals, m.p. 189° C.

We claim:

1. A compound selected from the group consisting of those of the formula:

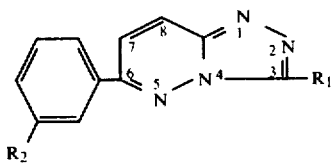

wherein $R_1$ is selected from the group comprising CHO, $CH_2Cl$, $CHCl_2$, $CCl_3$, $CH_2OH$, $CH_2O$-lower alkyl ($C_1$–$C_3$), $CH_2F$, $CHF_2$, $CF_3$, CN and $CO_2$-lower alkyl ($C_1$–$C_3$); $R_2$ is selected from the group consisting of hydrogen, fluoro, chloro and trifluoromethyl.

2. The compound according to claim 1, 3-(chloromethyl)-6-[3-(trifluoromethyl)phenyl]-1,2,4-triazolo[4,3-b]pyridazine.

3. The compound according to claim 1, 3-(chloromethyl)-6-phenyl-1,2,4-triazolo[4,3-b]pyridazine.

4. The compound according to claim 1, 3-(methoxymethyl)-6-phenyl-1,2,4-triazolo[4,3-b]pyridazine.

5. The compound according to claim 1, 3-(methoxymethyl)-6-[3-(trifluoromethyl)phenyl]-1,2,4-triazolo[4,3-b]-pyridazine.

6. The compound according to claim 1, 3-(hydroxymethyl)-6-[3-(trifluoromethyl)phenyl]-1,2,4-triazolo[4,3-b]-pyridazine.

* * * * *